(12) United States Patent
Namkoong

(10) Patent No.: US 7,466,428 B2
(45) Date of Patent: Dec. 16, 2008

(54) METHOD OF MEASURING THICKNESS OF THIN LAYER IN SEMICONDUCTOR DEVICE AND APPARATUS FOR PERFORMING METHOD

(75) Inventor: Whan Namkoong, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 351 days.

(21) Appl. No.: 11/475,933

(22) Filed: Jun. 28, 2006

(65) Prior Publication Data
US 2007/0019205 A1 Jan. 25, 2007

(30) Foreign Application Priority Data
Jul. 20, 2005 (KR) .................. 10-2005-0065878

(51) Int. Cl.
*G01B 11/02* (2006.01)
*G01B 11/28* (2006.01)
(52) U.S. Cl. ....................... 356/503; 356/630
(58) Field of Classification Search .......... 356/503, 356/504, 630, 632
See application file for complete search history.

(56) References Cited

U.S. PATENT DOCUMENTS

| | | | |
|---|---|---|---|
| 5,587,792 A * | 12/1996 | Nishizawa et al. ......... 356/504 |
| 6,465,265 B2 | 10/2002 | Opsal et al. | |
| 6,573,999 B1 * | 6/2003 | Yang ......................... 356/632 |
| 7,327,444 B2 * | 2/2008 | Naka et al. ................. 356/630 |
| 2004/0265477 A1 * | 12/2004 | Nabatova-Gabain et al. .. 427/10 |
| 2005/0041255 A1 * | 2/2005 | Hyun et al. ................. 356/504 |
| 2007/0281075 A1 * | 12/2007 | Huang ......................... 427/8 |

FOREIGN PATENT DOCUMENTS

JP   2003-203957   7/2003

* cited by examiner

*Primary Examiner*—Patrick J Connolly
(74) *Attorney, Agent, or Firm*—Volentine & Whitt, PLLC

(57) ABSTRACT

A method of measuring the thickness of a thin layer formed on a substrate comprises generating a measured signal spectrum by reflecting a light off of the thin layer and analyzing a resulting reflected light. The method further comprises generating a theoretical signal spectrum based on a putative thickness of the thin layer, and computing a skew signal spectrum as a difference between the measured signal spectrum and the theoretical spectrum. The method still comprises computing a reliability index by dividing a reference index by an area of the skew signal spectrum and using the reliability index to update the theoretical signal spectrum in a regression fitting process.

23 Claims, 11 Drawing Sheets

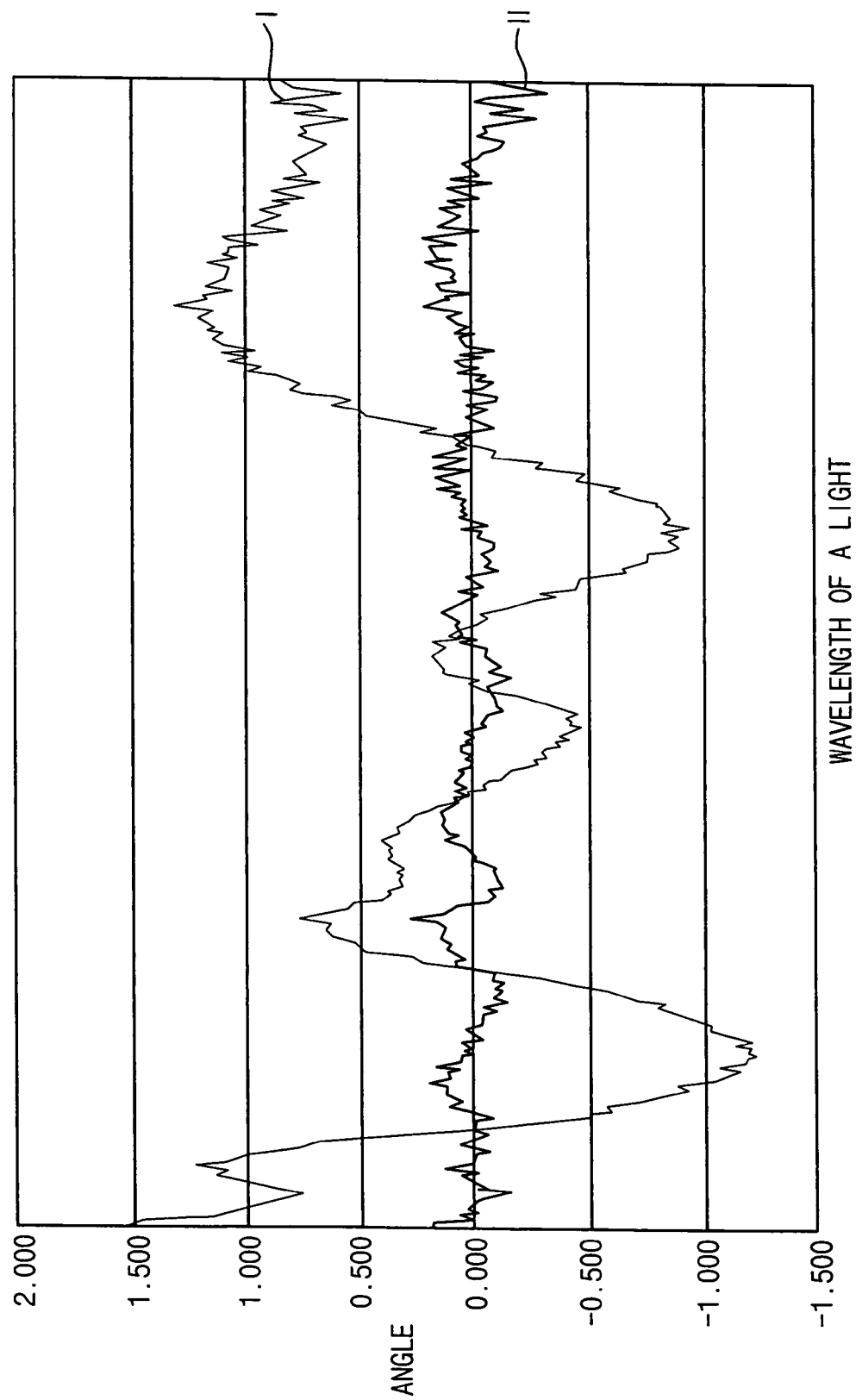

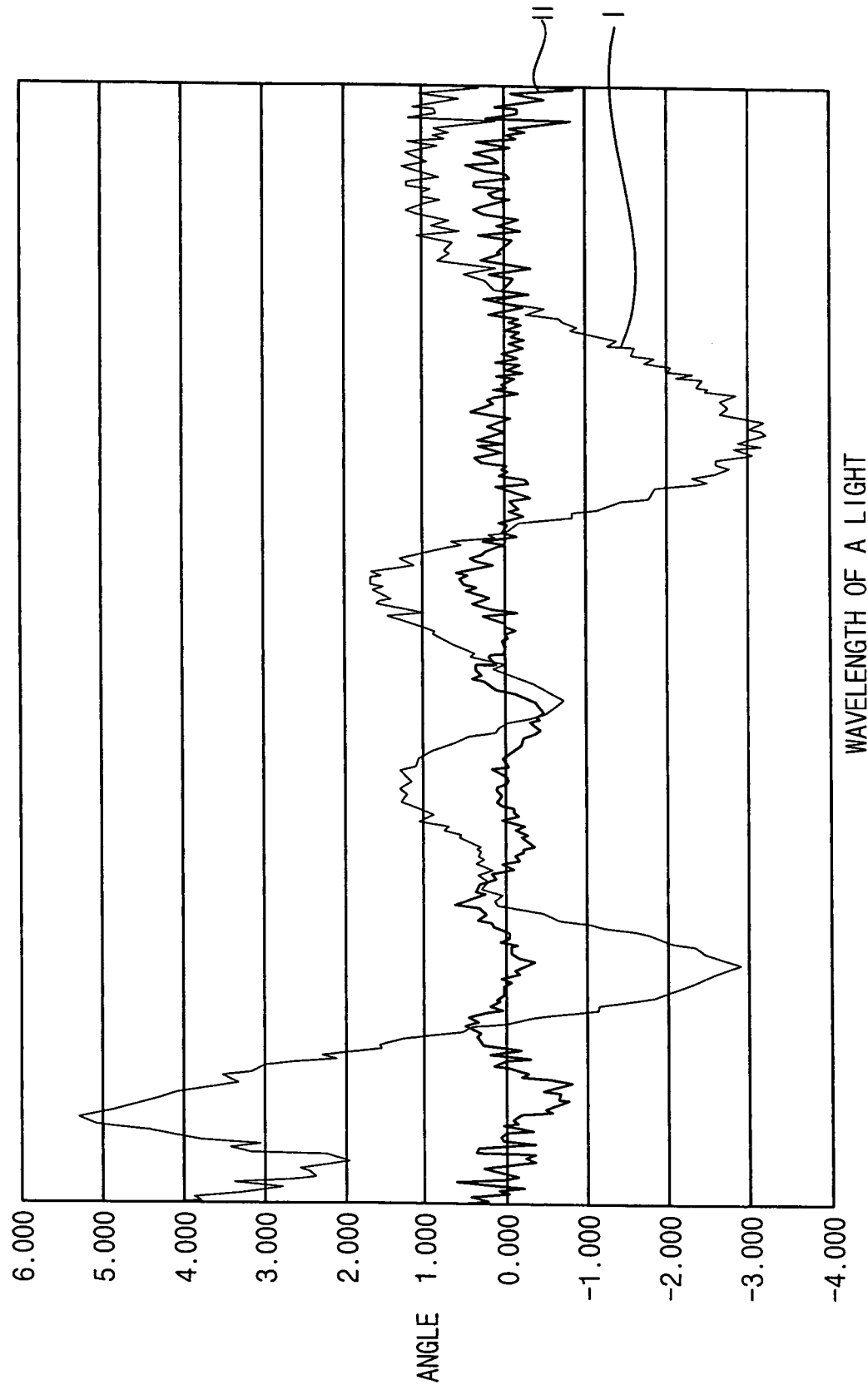

METHOD OF MEASURING THICKNESS OF THIN LAYER IN SEMICONDUCTOR DEVICE AND APPARATUS FOR PERFORMING METHOD

BACKGROUND OF THE INVENTION

1. Field of the Invention

Embodiments of the present invention relate generally to a method of measuring the thickness of a thin layer in a semiconductor device, and an apparatus for performing the method. More particularly, embodiments of the invention relate to a method and apparatus for measuring the thickness of a thin layer using a regression fitting process.

A claim of priority is made to Korean Patent Application No. 2005-65878, filed on Jul. 20, 2005, the disclosure of which is hereby incorporated by reference in its entirety.

2. Description of Related Art

Modern semiconductor devices tend to include several thin layers formed on a substrate. These thin layers are generally formed by performing several thin layer forming processes in sequence on the substrate. A typical semiconductor device includes, for example, an insulation layer, a dielectric layer, and a metal layer formed sequentially on a substrate such as a silicon wafer. In addition to the thin layer forming processes, patterning processes such as etching and photolithography are also performed to create patterns in the thin layers.

The physical characteristics of each thin layer, such as thickness, chemical composition, and optical coefficients (e.g., refractive index and extinction coefficient), can affect the way a semiconductor device performs. Moreover, the physical characteristics of each layer can affect the way that layers are subsequently formed and therefore how the subsequently formed layers behave. As a result, semiconductor manufacturers like to monitor the physical characteristics of thin layers as they are formed to ensure the quality of the semiconductor devices.

Monitoring the physical characteristics of each layer in a semiconductor device becomes more important as the integration density of the device increases because as the features of a semiconductor device become smaller, it becomes more likely that small variations in the physical characteristics of each thin layer will affect the device's performance. One example of how small variations in the physical characteristics of a thin layer can affect a device's performance is provided by a gate oxide layer used to form a transistor. Where the gate oxide layer is too thin, it may break down under normal operating conditions, corrupting the device.

One way to measure the physical characteristics of a thin layer involves forming the thin layer on a wafer and then cutting the wafer into a plurality of specimens that can be analyzed using an electron-based imaging apparatus such as a vertical scanning electron microscope (VSEM). Unfortunately, this method is both costly and time consuming, and as a result, researchers have developed other "non-destructive" techniques, i.e., techniques that do not require cutting up a wafer, for measuring the physical characteristics of a thin layer.

Several of the non-destructive techniques rely on optical technology to measure the physical properties of thin layers. However, because layers formed beneath the thin layer can create optical distortion, e.g., in the form of interference, the optical techniques are generally not applied to a working wafer where a semiconductor device is formed. Instead, these techniques are commonly applied to a monitoring wafer on which a thin layer is formed using the same thin layer processes performed on the working wafer. Then, the measurements obtained from the monitoring wafer are used to infer the properties of the thin layer formed on the working wafer.

Unfortunately, conventional optical technologies for measuring the physical characteristics of a thin layer still suffer from a variety of inaccuracies and inefficiencies. For example, characteristics inferred from measurements performed on the monitoring wafer may not accurately reflect the true characteristics of the thin layer on the working wafer. In addition, processes for forming a thin layer on the monitoring wafer increase the time and cost of manufacturing a semiconductor device.

To address the drawbacks of these conventional approaches, a dual beam spectrometry process and a spectroscopic ellipsometry process have been developed to measure the thickness of a thin layer formed in a multilayer structure including a plurality of thin layers.

Both the dual beam spectrometry process and the spectroscopic ellipsometry process can use a combination of measured values and theoretical values to generate estimates for the physical properties of a thin layer. For instance, the thickness of the thin layer can be computed by obtaining measurements related to the thickness and then finding a theoretical function that is a "best fit" to the measurements. The theoretical function is generated from a putative thickness of a hypothetical layer. The putative thickness (also called "presumptive" thickness or "assumed" thickness) is a temporary thickness estimate used in the estimation process. Eventually, the putative thickness is stored as an "actual" thickness. The putative thickness that corresponds to the "best fit" function is then generated as the estimate of the thin layer's thickness. An example of a spectroscopic ellipsometry process that uses theoretical and measured values to generate an estimate of the thickness of a thin layer in a semiconductor device is described briefly below.

In the spectroscopic ellipsometry process, polarized light is reflected off of the thin layer and then various properties of the reflected light are measured and used to estimate the thickness of the layer. In particular, a spectroscopic ellipsometer measures an amplitude change and a phase shift of the reflected light as a function of the light's various wavelengths. These measurements, also called measured signals, are collected for a range of wavelengths contained in the polarized light to generate a "measured signal spectrum" for the thin layer. The amplitude change and phase shift are used to determine a reflectance ratio defined as an intensity of a first reflected component that oscillates parallel to a plane of incidence divided by the intensity of a second reflected component that oscillates parallel to a plane of a sample surface of the thin layer. Due to their respective orientations relative to the surface of the thin layer, the first reflected component will be referred to as a vertical component and the second reflected component will be referred to as a horizontal component.

In general, a thin layer with a known thickness has a corresponding "theoretical signal spectrum" which one would expect to match with the layer's measured signal spectrum. For a given measurement process, there is typically a mapping between the thickness and the theoretical signal spectrum such that if either the thickness or the theoretical signal spectrum is known, the other can be inferred or derived. Because measurements are rarely one hundred percent precise, the theoretical signal spectrum of a thin layer with a known thickness may vary from the thin layer's measured signal spectrum. Accordingly, where the measured signal spectrum of a thin layer is known, a corresponding theoretical signal spectrum can be identified as the theoretical signal spectrum that best approximates the measured signal spectrum. A thickness of the thin layer can then be derived from the identified theoretical signal spectrum.

FIGS. 1A and 1B show concrete examples of theoretical and measured signal spectra obtained by reflecting polarized light off of a thin layer using a spectroscopic ellipsometer manufactured by Nanometrics. The polarized light is reflected off of the thin layer at an angle of 65°. In FIGS. 1A and 1B, the theoretical signal spectra are denoted by solid curves and the measured signal spectra are denoted by dotted curves.

In FIG. 1A, various wavelengths of the reflected light are plotted against an inverse tangent of the reflectance ratio of the vertical and horizontal components. In FIG. 1B, various wavelengths of the reflected light are plotted against a phase change of the reflected light. The inverse tangent of the reflectance ratio and the phase change were calculated based on ellipsometry theory.

A conventional approach to measuring the similarity between the measured signal spectrum and the theoretical spectrum is a "goodness of fit" (GOF) criteria based on a mean square error (MSE) function in statistics. The MSE is based on a difference between the measured signal spectrum and the theoretical signal spectrum. The difference between the measured signal spectrum and the theoretical signal spectrum is referred to in this description as a "skew signal spectrum" and the difference between a measured signal and a corresponding theoretical signal defined with respect to the same wavelength is referred to as a "skew signal."

For a measured signal spectrum/theoretical signal spectrum pair, the GOF criteria defines a GOF value between zero (0) and one (1). Where the measured signal spectrum and the theoretical signal spectrum are the same, the GOF value is one (1). As the dissimilarity between the measured and theoretical signal spectra increases, the GOF value tends toward zero. Unfortunately, the GOF value may not accurately reflect the level of similarity between the measured signal spectrum and the theoretical spectrum.

For example, in FIGS. 1A and 1B, the measured signal spectrum and the theoretical signal spectrum are visibly dissimilar from each other, but the GOF value is about 0.976, which is relatively high. Conventional optimization techniques could be used to further increase the GOF value to about 0.99.

The way to maximize the GOF value between a theoretical signal spectrum and the measured signal spectrum is to find a theoretical signal spectrum as close to the measured signal spectrum as possible. One way to do this is by a "regression fitting process." In the regression fitting process, a putative thickness for the thin layer is chosen and then the theoretical signal spectrum is computed based on the putative thickness. Then, the GOF value is computed for the theoretical signal spectrum and the measured signal spectrum. If the GOF value is above a predetermined threshold, the putative thickness is assumed to be the actual thickness of the thin layer. However, if the GOF value is below the predetermined threshold, the putative thickness is updated and the process of computing the theoretical spectrum is repeated.

Because the GOF value is based on the difference between the theoretical signal spectrum and the measured signal spectrum, the GOF value tends to be relatively high if the measured signal spectrum has a simple shape or is distributed over a small range. This is true even if the actual shapes of the theoretical and measured signal spectra differ significantly since the actual difference between two curves both distributed over a small range is generally small. However, where the measured and theoretical signal spectra are distributed over a large range and have a complicated shape, the GOF value may be small even if the theoretical and measured signal spectra appear to be very similar. FIG. 2 and FIGS. 3A and 3B demonstrate a relationship between the GOF value and the range of the theoretical and measured signal spectra.

FIG. 2 is a view illustrating the measured and theoretical signal spectra of a light reflected from a thin layer formed to a thickness of about 15,000 Å on a wafer. The experimental conditions for the results shown in FIG. 2 are the same as the conditions for the experimental results shown in FIGS. 1A and 1B. FIG. 2 shows a graph of the inverse tangent of a reflectance ratio of the vertical and horizontal components of the reflected light as a function of the wavelength of the light. In FIG. 2, the measured and theoretical signal spectra are almost identical to each other and their GOF value is about 0.976. No matter how many times the conventional regression fitting process is repeated on the data shown in FIG. 2, their GOF value will not exceed 0.976. Accordingly, FIGS. 1A and 1B and FIG. 2 demonstrate that the same GOF value may indicate very different levels of similarity depending on the range and shape of the measured signal spectrum.

The measured signal spectrum in FIG. 1B ranges between about 20 and 27, while the measured signal spectrum in FIG. 2 ranges from about 20 to 80. While the measured signal spectrum in FIG. 1B has a relatively simple shape, the measured signal spectrum in FIG. 2 has a relatively complicated shape.

FIG. 3A shows a skew signal spectrum for the theoretical and measured signal spectra in FIG. 1A, and FIG. 3B shows a skew signal spectrum for the theoretical and measured signal spectra in FIG. 2. Even though the measured and theoretical signal spectra in FIG. 2 appear to be more similar than the measured and theoretical signal spectra in FIG. 1A, the ranges of their respective skew signal spectra are very similar.

The skew signal spectrum shown in FIG. 3A is the result of a poor regression fitting process, and the skew signal spectrum shown in FIG. 3B is the result of a good regression fitting process. However, in both cases, the range of the skew signal spectrum is small, and therefore the GOF value is close to one (1). In particular, the skew signal spectrum shown in FIG. 3A has a maximum value of about +1.534 and a minimum value of about −1.226 and the skew signal spectrum shown in FIG. 3B has a maximum value of about +1.285 and a minimum value of about −1.319. Since the GOF criteria does not distinguish a poor regression fitting process from a good regression fitting process, an improved measure of the similarity between the measured and theoretical signal spectra is desired.

SUMMARY OF THE INVENTION

According to one embodiment of the invention, a method of measuring a thickness of a target thin layer formed on a substrate is provided. The method comprises generating a reference skew signal spectrum by performing a regression fitting process on data produced with respect to a reference thin layer formed on a reference layer. The method further comprises generating a reference index by processing the reference skew signal spectrum, generating a measured signal spectrum by irradiating a first light off of the target thin layer to produce a first reflected light, and then analyzing the first reflected light, and generating a theoretical signal spectrum based on a putative thickness of the target thin layer and physical properties of the target thin layer. The method still further comprises generating a target skew signal spectrum as a difference between the measured signal spectrum and the theoretical signal spectrum, computing a reliability index based on the reference index and the target skew signal spectrum, determining whether the reliability index is within a predetermined first desired range, and selecting the putative thickness of the target thin layer as an actual thickness of the target thin layer if the reliability index is within the first desired range.

According to another embodiment of the invention, an apparatus for measuring a thickness of a target thin layer formed on a substrate is provided. The apparatus comprises a storing unit adapted to store recipe data including a reference index and a putative thickness of the target thin layer, wherein the reference index is derived from a regression fitting process performed on data obtained with respect to a reference thin layer formed on a reference wafer. The apparatus further comprises a measured signal generating unit adapted to generate a measured signal spectrum by irradiating a first light on the target thin layer to produce a first reflected light and analyzing the first reflected light, a theoretical signal generating unit adapted to generate a theoretical signal spectrum using a theoretical calculation whose inputs include a putative thickness of the target thin layer, a skew generating unit adapted to generate a target skew signal spectrum as a difference between the measured signal spectrum and the theoretical signal spectrum, and a processing unit comprising a processing element adapted to calculate a reliability index from the target skew signal spectrum and the reference index, and a selector adapted to select the putative thickness of the target thin layer as an actual thickness of the target thin layer when the reliability index is within an predetermined desired range.

BRIEF DESCRIPTION OF THE DRAWINGS

The invention is described below in relation to several embodiments illustrated in the accompanying drawings. Throughout the drawings like reference numbers indicate like exemplary elements, components, or steps. In the drawings:

FIG. 10A is a graph illustrating skew signal spectra corresponding to measured and theoretical spectra shown in FIGS. 1A and 9A; and, FIG. 10B is a view illustrating skew signal spectra corresponding to measured and theoretical spectra shown in FIGS. 1B and 9B.

DESCRIPTION OF EXEMPLARY EMBODIMENTS

Exemplary embodiments of the invention are described below with reference to the corresponding drawings. These embodiments are presented as teaching examples. The actual scope of the invention is defined by the claims that follow.

In this written description, elements described as being "on," "connected to," or "coupled to" another element or layer can be directly on, connected or coupled to the other element or layer, or intervening elements or layers may be present. However, when an element is referred to as being "directly on," "directly connected to," or "directly coupled to" another element or layer, there are no intervening elements or layers present. The term "and/or" is used to refer to any or all combinations of one or more items in a list.

Figure 4:
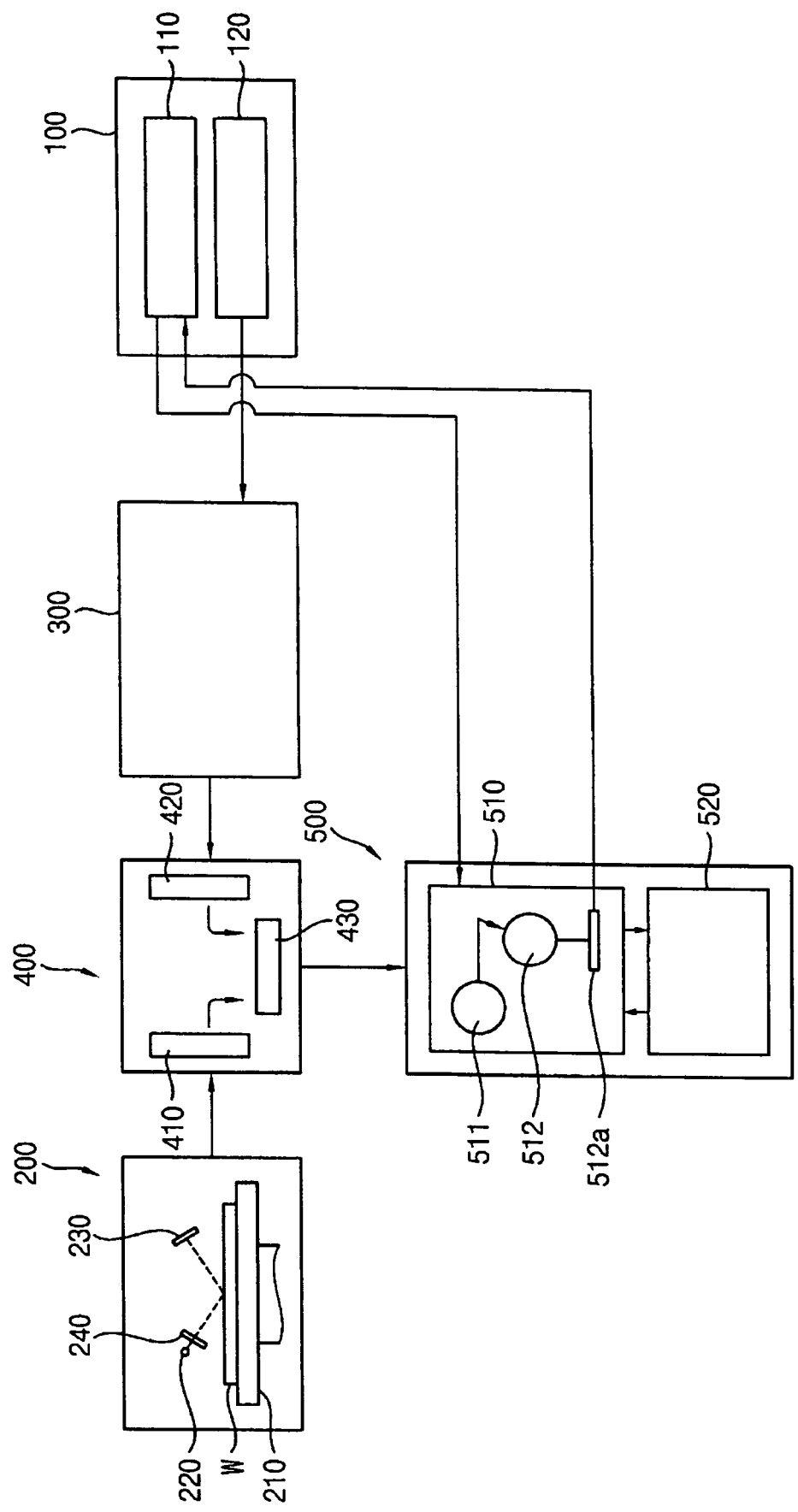
FIG. 4 is a diagram illustrating an apparatus for measuring a thickness of a thin layer formed on a substrate according to an exemplary embodiment of the present invention.

FIG. 4 is a schematic view illustrating an apparatus for measuring a thickness of a target thin layer formed on a substrate such as a wafer in accordance with an exemplary embodiment of the present invention. Referring to FIG. 4, the measurement apparatus comprises a storing unit 100, a measured signal generating unit 200, a theoretical signal generating unit 300, a skew generating unit 400, and a processing unit 500.

Storing unit 100 stores recipe data used to generate a theoretical spectrum for measuring the thickness of the target thin layer. For example, the recipe data typically includes a putative thickness of the target thin layer, a refractive index "n" of the target thin layer, and an extinction coefficient "k" of the target thin layer. The recipe data also typically includes a reference index, which is generated by a regression fitting process performed on a reference theoretical signal spectrum and a reference measured signal spectrum generated with respect to a reference thin layer formed on a reference wafer. The reference index is generated as the area of a reference skew signal spectrum, which is defined as a difference between the reference measured signal skew spectrum and the reference theoretical signal spectrum.

Theoretical signal generating unit 300 generates a plurality of theoretical signals based on the putative thickness of the target thin layer. The plurality of theoretical signals correspond to different wavelengths of light in a light irradiated on a working wafer "W" in measured signal generating unit 200. Skew generating unit 400 generates target skew signals based on respective differences between measured signals generated by measured signal generating unit 200 and the corresponding theoretical signals. Processing unit 500 aggregates the target skew signals into a target skew signal spectrum and then computes an area of the target skew signal spectrum as a fitting index.

The area of the target skew signal spectrum or the reference skew signal spectrum can be computed in a variety of ways. One way is to compute the absolute value of the integral or sum of the target or reference skew signal spectrum. Another way is to compute the integral or sum of the absolute value of the target or reference skew signal spectrum so that the area is always positive. In either case, the area is a positive quantity related to a space between the skew signal spectrum and the x-axis.

Storing unit 100 comprises a first storage element 110 for storing a first recipe including the reference index, and a second storage element 120 for storing a second recipe including the putative thickness of the target thin layer.

The reference skew signal is generated by forming a reference thin layer on a reference wafer using the same thin layer forming processes used to form a thin layer on a working wafer "W" in measured signal generating unit 200. Typically, the reference wafer is one of a plurality of wafers where thin layers are formed under the same or similar processing conditions. The reference thin layer is assigned a putative reference thickness, and the reference theoretical signal spectrum is computed based on the putative reference thickness. The reference measured signal spectrum is generated using a spectroscopic ellipsometry process. A regression fitting process is then performed wherein the putative reference thickness is updated until a corresponding reference skew signal indicative of a difference between the reference theoretical signal spectrum and the reference measured signal spectrum has a value below a predetermined threshold.

Measured signal generating unit 200 comprises a support 210 for supporting working wafer "W," where the target thin layer is formed, a light source 220 for irradiating a light onto the target thin layer, a polarizer 240 for polarizing the light before it arrives at working wafer "W", and a signal generator 230 for detecting reflected light from the target thin layer and generating a plurality of measured signals corresponding to various wavelengths of the reflected light.

Support 210 comprises a flat plane located in a processing chamber. Working wafer "W" is loaded into the processing chamber and secured to support 210. Light source 220 then irradiates light onto working wafer "W" at a predetermined angle. The light passes through polarizer 240 and reflects off of working wafer "W" to produce reflected light. The reflected light is detected and analyzed by signal generator 230, and then signal generator 230 generates measured signals for various wavelengths of light in the reflected light. Collectively, the measured signals form a measured signal spectrum.

Signal generator 230 includes a detector (not shown) for detecting the reflected light, a decomposer (not shown) for decomposing the reflected light into a vertical component and a horizontal component, and a signal processor (not shown) for generating first and second measured signals by processing the vertical and horizontal components.

In one embodiment of the invention, the first measured signal is generated as an inverse tangent of a reflectance ratio, $\tan^{-1}\psi$, between the vertical and horizontal components of the reflected light and the second measured signal is generated as a phase difference $\Delta$ between the vertical and horizontal components of the reflected light. The first and second measured signals are expressed as degrees of an angle and are arranged in accordance with the wavelength of the light.

Signal generator 230 may generate other signals associated with optical measurement technology. For example, signal generator 230 may generate a measured signal indicative of a reflectance of the light as in a dual beam spectrometer. Where different optical technologies such as dual beam spectrometry are used, polarizer 240 may be omitted.

The first recipe stored in first storage element 110 generally includes the reference index. The second recipe stored in second storage element 120 typically the putative thickness of the target thin layer, refractive index "n," and extinction coefficient "k". The second recipe may further include other data used or produced in association with various optical measurement technologies.

Measured signal generating unit 200 generates measured signal spectrum based on the properties of the light reflected off of the target thin layer. The measured signal spectrum is typically formed by generating a plurality of measured signals corresponding to different wavelengths of the light produced by light source 220. In one embodiment, measured signal generating unit 200 includes or is part of an ellipsometer adapted to measure the thickness of thin layers using polarized light. However, measured signal generating unit 200 may also include other conventional optical measurement technologies for measuring the thickness of the thin layer.

Polarizer 240 may be omitted from measured signal generating unit 200 depending on the type of optical measurement technology used therein. For example, polarizer 240 is not required where the optical measurement technology does not use polarized light. Furthermore, depending on the type of optical measurement technology used in measured signal generating unit 200, it may not be necessary to irradiate the light onto working wafer "W" at an angle. Instead, it may be possible to irradiate the light perpendicular to wafer "W". The light is generally irradiated onto wafer "W" at an angle when measured signal generating unit 200 uses an ellipsometer to generate the measured signal spectrum.

Theoretical signal generating unit 300 generates theoretical signals using a computer simulation based on a particular optical measurement theory such as ellipsometry theory. Theoretical signal generating unit 300 generates the theoretical signal spectrum by generating a plurality of theoretical signals as a function of various wavelengths of light in the irradiated light. The theoretical signal spectrum is later compared with the measured signal as part of the regression fitting process.

Where the optical measurement theory used to generate the theoretical signal spectrum is ellipsometry theory, the inputs to the computer simulation are the putative thickness of the target thin layer, the refraction index "n", and the extinction coefficient "k." The computer simulation generally computes the theoretical signal spectrum using an algorithm stored in the measurement apparatus. The putative thickness, the refraction index "n", and the extinction coefficient "k" are typically transferred to the computer simulation from second storage element 120.

Skew generating unit 400 calculates a numerical difference between the measured signal spectrum produced by measured signal generating unit 200 and the theoretical signal spectrum produced by theoretical signal generating unit 300 and generates the target skew signal spectrum as the numerical difference. Skew generating unit 400 comprises a first input element 410 into which the measured signal spectrum is input from measured signal generating unit 200, a second input element 420 into which the theoretical signal spectrum is input from theoretical signal generating unit 300, and a subtraction element 430 for generating the target skew signal spectrum by subtracting the theoretical signal spectrum from the measured signal spectrum. The measured and theoretical signal spectra are defined over the same set of wavelengths so that the target skew signal spectrum is also defined over the same set of wavelengths.

In general, the target skew signal spectrum is composed of a plurality of skew signals, each generated by as the difference between a measured signal from a theoretical signal generated for a particular wavelength of light. After the target skew signals are generated, these signals can be grouped together to form the target skew signal spectrum in processing unit 500. In other words, it is not necessary for the entire measured signal spectrum or theoretical signal spectrum to be present in first or second input unit 410 or 420 to generate the target skew signal spectrum—the target skew signal spectrum can be generated as multiple target skew signals.

Processing unit 500 computes an actual thickness of the target thin layer using the target skew signal spectrum and the reference index. Processing unit 500 includes a processing element 510 for calculating the reliability index using the target skew signal spectrum and the reference index, and a selector 520 for selecting the putative thickness as the actual thickness of the thin layer when the reliability index is within a desired range. The reliability index is typically computed as the reference index, which is the area of the reference skew signal spectrum, divided by the fitting index, which is the area of the target skew signal spectrum.

Processing element 510 comprises a skew signal processor 511 for generating the fitting index, and an index calculator 512 for generating the reliability index as the ratio of the reference index and the fitting index.

The target skew signal spectrum is typically formed by aggregating target skew signals output from subtraction element 430 over a plurality of wavelengths of light in skew signal processor 511. Like the measured and theoretical signal spectra, the target skew signal spectrum can be represented as a graph in a rectangular coordinate system with the wavelength of light on the x-axis.

Skew signal processor 511 may include, for example, an integrator (not shown) for computing the sum or integral using a numerical method. A first predetermined wavelength of light may be assigned as an initial point of an integration interval and a second predetermined wavelength of the light may be assigned as a final point of the integration interval, and the numerical method may compute the area under the absolute value of the target skew signal spectrum by integrating over the integration interval. Instead of integrating the absolute value of the target skew signal spectrum, skew signal processor 511 may instead integrate the target skew signal spectrum and then take the absolute value of the result.

Index calculator 512 calculates the reliability index using the reference index stored in first storage element 110 and the fitting index transferred from the skew signal processor 511. The reliability index indicates a desired similarity between the theoretical signal and the measured signal.

The reliability index is typically computed as a ratio of the reference index and the fitting index. Where the theoretical signal spectrum is identical to the measured signal spectrum, the area of the target skew signal spectrum is identical to the area of the reference skew signal spectrum, and therefore the reference index is the same as the fitting index. In other words, where the theoretical signal spectrum is identical to the measured signal spectrum, the reliability index is one. In contrast, where the theoretical signal spectrum is different from the measured signal spectrum, the area of the target skew signal spectrum tends to be larger than that of the reference skew signal spectrum because the reference measured signal spectrum tends to be a relatively close approximation to the reference theoretical signal spectrum. Where the theoretical signal spectrum is significantly different from the measured signal spectrum, the reliability index approaches zero.

Where the area of the target skew signal spectrum is smaller than the area of the reference skew signal spectrum, the reliability index can exceed one. Under these conditions, the theoretical signal spectrum and the measured signal spectrum are more similar than the reference theoretical signal spectrum and the reference measured signal spectrum. In such a case, the reference index is replaced by the fitting index. Index calculator 512 further includes a skew transfer element 512a for transferring the area of the target skew signal spectrum into first storage element 110 when the reliability index is greater than one. As a result, the reliability index will always be a number between zero and one. However, the scale of the reliability index may be enlarged to facilitate its usage. For example, the reliability index may be expressed as percentage units by multiplying the scale size by 100.

Selector 520 determines whether the reliability index is within the desired range. Where the reliability index is within the desired range, the selector selects the putative thickness as the actual thickness of the target thin layer. Where the reliability index is not within the desired range, the putative thickness of the target thin layer is updated and a new theoretical signal is calculated using the updated putative thickness, the refraction index "n" and the extinction coefficient "k". The comparison process is performed again to measure the similarity between the measured signal spectrum and the theoretical signal spectrum. The processes of updating the putative thickness, recalculating the theoretical signal spectrum, and comparing the recalculated theoretical signal spectrum are repeated until the reliability index is within the desired range. Once the reliability index is within the desired range, the putative thickness is selected as the actual thickness of the target thin layer. The desired range for the reliability index is typically stored in an additional storage element (not shown) in the measurement apparatus, and transferred into selector 520 whenever the area of the target skew signal spectrum is calculated. In some embodiments of the invention, a human operator checks the reliability index and the putative thickness after selected iterations of the regression fitting processes and controls the desired range.

The reliability index is typically defined as a ratio of the area of the reference skew signal spectrum and the area of the target skew signal spectrum. The reliability index is used instead of the conventional GOF criteria, which is based solely on the area of the target skew signal spectrum. Using the reliability index in this way significantly improves, the reliability of the regression fitting process for measuring the thickness of a target thin layer. Further, the reliability index may be used to evaluate the accuracy with which the putative thickness approximates the true thickness of the target thin layer.

A method of measuring the thickness of a thin layer formed on a wafer in the above-described apparatus is described below in relation to FIGS. 4 to 8. In the description that follows, exemplary method steps are denoted by parentheses (XXX) to distinguish them from exemplary system elements such as those shown in FIG. 4.

Figure 5:
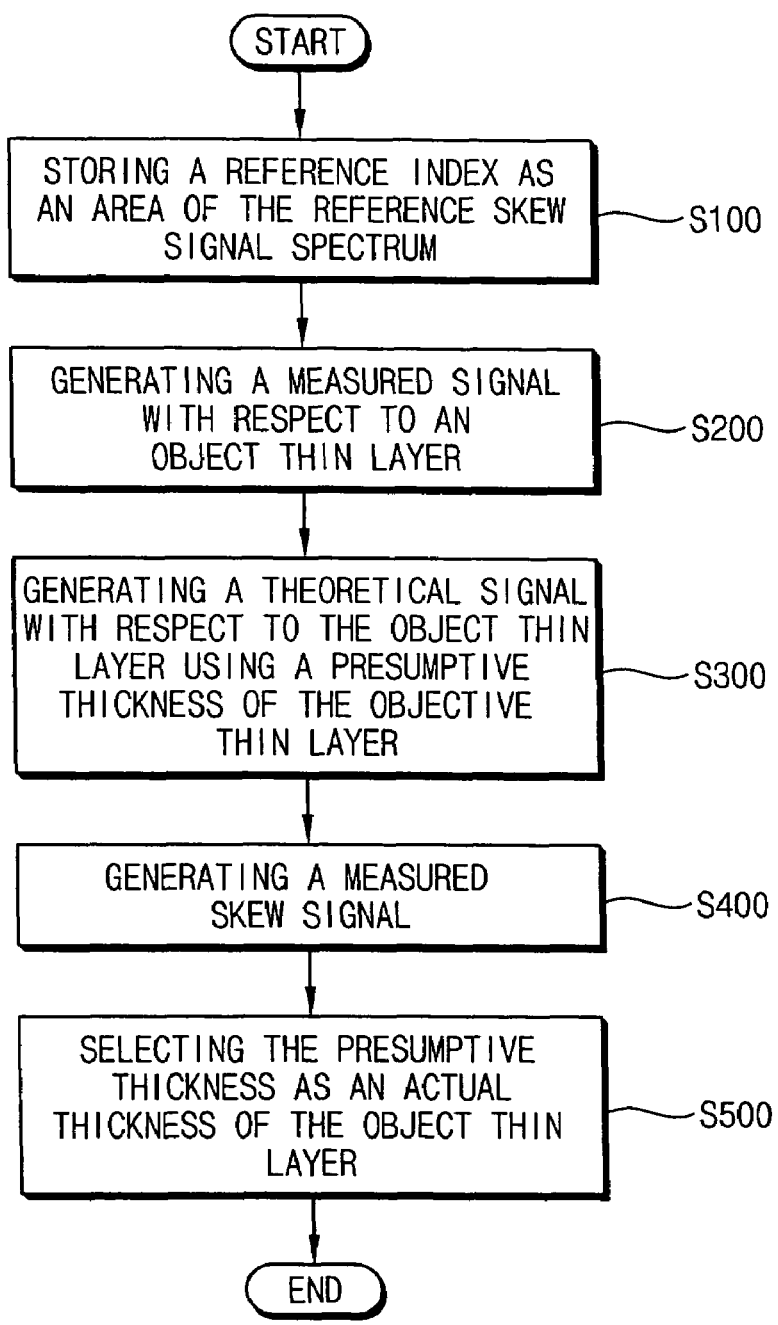
FIG. 5 is a flow chart illustrating a method of measuring a thickness of a thin layer formed on a substrate according to an exemplary embodiment of the present invention.
Figure 6:
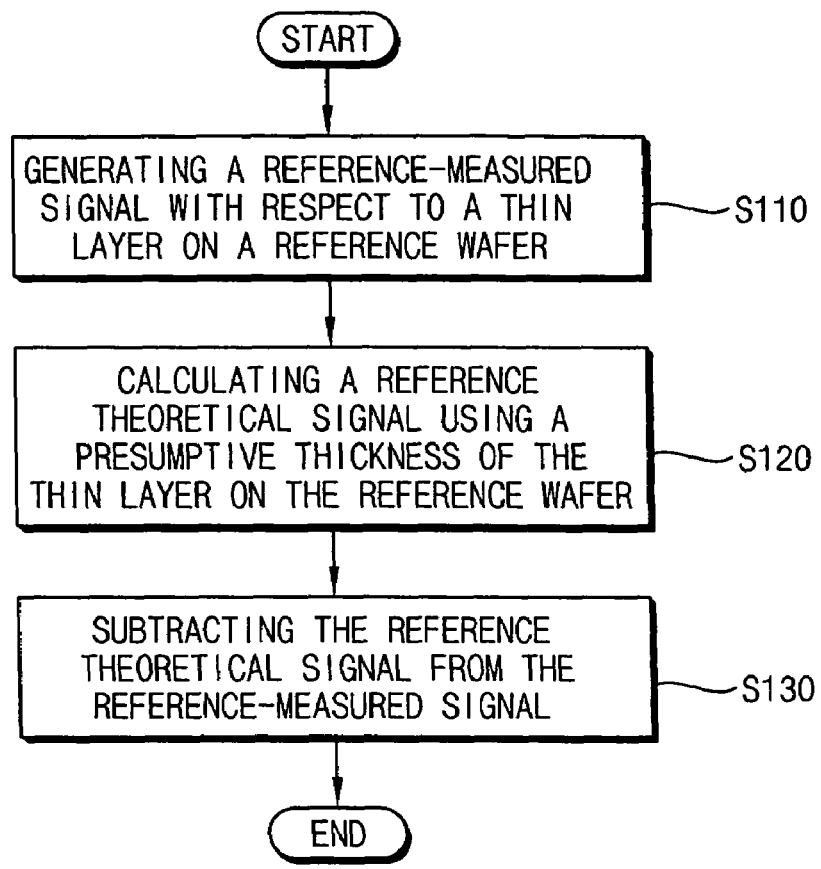
FIG. 6 is a flow chart illustrating step S100 of the method illustrated in FIG. 5 in further detail.
Figure 7:
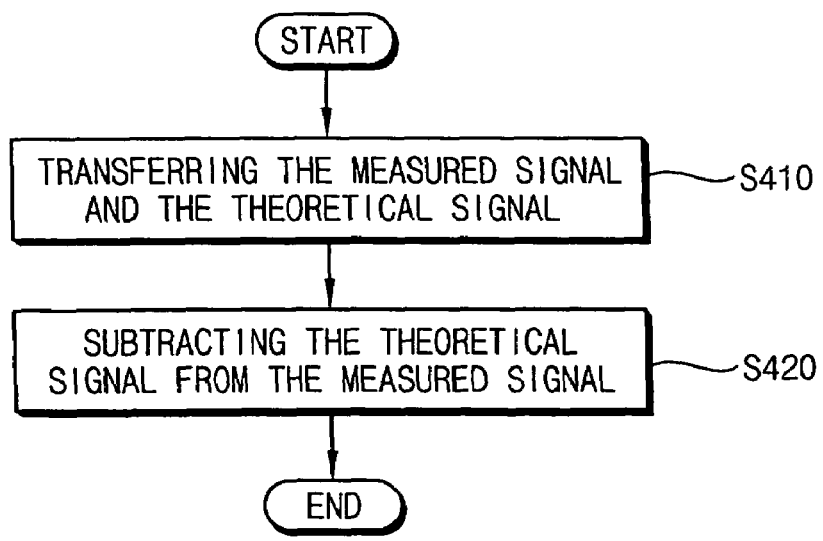
FIG. 7 is a flow chart illustrating step S400 of the method illustrated in FIG. 5 in further detail.
Figure 8:
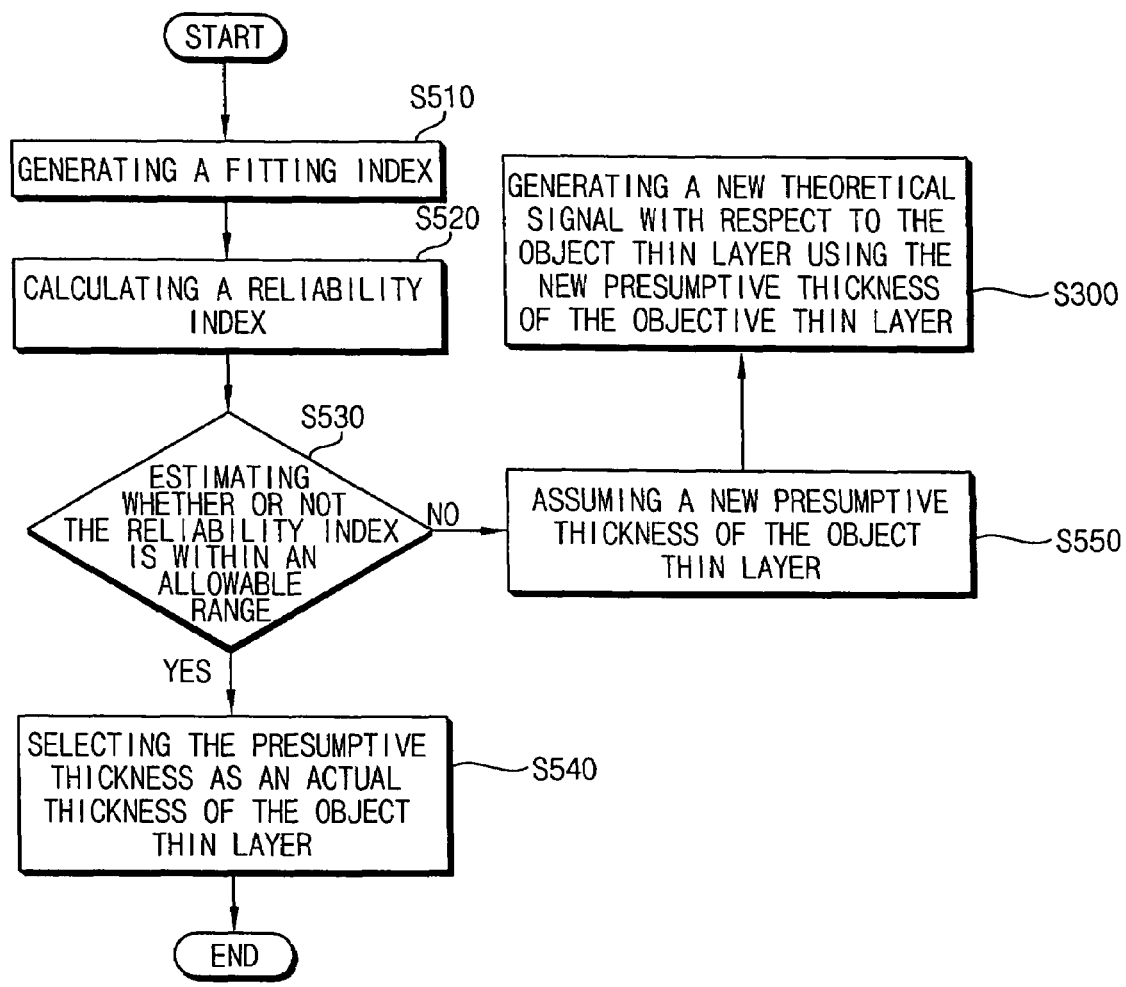
FIG. 8 is a flow chart illustrating step S500 of the method illustrated in FIG. 5 in further detail.

FIG. 5 is a flow chart illustrating a method of measuring the thickness of a thin layer formed on a wafer according to an exemplary embodiment of the present invention, and FIGS. 6 through 8 are a flow charts illustrating various steps in the method of FIG. 5 in further detail.

Referring to FIGS. 4 through 8, the reference index is stored in first storage element 110 as a recipe for measuring the thickness of the target thin layer formed on working wafer "W" (S100).

The reference index is typically calculated in a conventional measurement apparatus. A thin layer is formed on a plurality of sample wafers under a uniform set of conditions. The sample wafers include the reference wafer on which the reference thin layer is formed, as described above. In addition, the sample wafers also include working wafer "W" on which the target thin layer is formed. The thin layer formed on the plurality of sample wafers includes the reference thin layer and the target thin layer. The reference wafer is loaded into the conventional measurement apparatus to obtain the reference index. To obtain the reference index, first, light is irradiated onto a surface of the reference thin layer. Light reflected off the reference thin layer is then detected and analyzed in the conventional measurement apparatus. A reference measured signal is then generated based on the reflected light, and the measured signal is stored in the measurement apparatus (S110).

A reference theoretical signal is calculated using a putative thickness (hereafter, reference putative thickness) of the reference thin layer and some physical quantities related to the reference thin layer. The reference theoretical signal is calculated using a known optical measurement theory (S120). Next, a comparison process is performed to detect a level of similarity between the reference measured signal and the reference theoretical signal. Where the similarity between the reference measured signal and the reference theoretical signal is within a desired range, the putative thickness and the physical quantities are stored in second storage element 120 as a second recipe. Where the similarity between the reference measured signal and the reference theoretical signal is not within the desired range, the reference putative thickness is updated and a modified reference theoretical signal is calculated based on the updated reference putative thickness using the optical measurement theory. The process of updating the reference putative thickness and recalculating the reference theoretical signal is repeated until the similarity between the reference theoretical signal and the reference measured signal is within a desired range.

A reference skew signal is calculated by subtracting the reference theoretical signal from the reference measured signal (step S130). In addition, a reference skew signal spectrum can be formed by calculating a plurality of reference skew signals for various wavelengths of the light reflected off of the reference thin layer, and then aggregating the plurality of reference skew signals into a function based on the wavelengths to form the reference skew signal spectrum. The area of the reference skew signal spectrum is stored in first storage element 110 as the first recipe. In some embodiments of the present invention, the desired range for determining the reference index is set on the basis of the conventional GOF criteria.

The reference index is used to calculate a reliability index used in a regression fitting process for detecting the thickness of the target thin layer. The second recipe includes refractive index "n" and extinction coefficient "k" of the target thin layer. The area of the reference skew signal spectrum is used as the reference index for calculating the reliability index. The second recipe may further include other quantities used to perform measurements with optical measurement technology.

Once the first and second recipes are stored in storing unit 100, working wafer "W" is loaded into measured signal generating unit 200, and a measured signal is generated by reflecting light off of the target thin layer using light source 220 (S200). As described previously, measured signal generating unit 200 typically includes or is part of an ellipsometer, and the light typically comprises polarized light. However, measured signal generating unit 200 may include other devices for measuring the thickness of the object thin layer based on different optical measurement technologies. For example, measured signal generating unit 200 could includes a reflection light analyzer of a dual beam spectrometer using a reflectance of light.

Working wafer "W" is loaded onto support 210 and secured thereto, and light is irradiated onto a surface of the target thin layer from light source 220. The light is then reflected from the surface of the target thin layer and the reflected light is detected by signal generator 230. Signal generator 230 analyzes the reflected light to generate a measured signal which indicates measured properties of the target thin layer.

The light produced by light source 220 typically passes through a polarizer 240 so that it is polarized when it irradiates onto the target thin layer. In addition, the light is typically irradiated onto the target thin layer at a predetermined angle with respect to the surface of working wafer "W." The light reflects off of the target thin layer and is then detected by a detector and decomposed into a vertical component and a horizontal component. The vertical and horizontal components of the reflected light are processed in a signal processor to generate first and second measured signals.

Typically, the first measured signal comprises an inverse tangent of a reflectance ratio $\tan^{-1}\psi$ of the vertical and horizontal components of the reflection light and the second measured signal includes a phase difference A between the vertical and horizontal components of the reflection light. The first and second measured signals are expressed in degrees of an angle and are arranged in accordance with the wavelength of the light.

The measured signals generated by the signal processor may include additional quantities depending on the type of optical measurement technology used by the measurement apparatus. For example, the signal processor could generate a reflectance of the light as the measured signal where the measurement apparatus includes a dual beam spectrometer.

A theoretical signal is generated by signal generating unit 300 using the putative thickness of the target thin layer and the physical quantities stored in storing unit 100 (S300). The theoretical signal is generated by a computer simulation based on an optical measurement theory. A plurality of theoretical signals can be generated in this way for different wavelengths of light in order to form a theoretical signal spectrum.

The theoretical signal is typically generated using a computer simulation that applies ellipsometry theory. The simulation typically takes for its inputs the putative thickness of the target thin layer, the refraction index "n", and the extinction coefficient "k."

Similar to the theoretical signal spectrum, the measured signal spectrum comprises a plurality of measured signals generated for various wavelengths of light in the reflected light.

A numerical difference between respective measured and theoretical signals is calculated to generate target skew signals (S400). For various wavelengths of light in the reflected light, a corresponding measured signal is transferred to first input element 410 from measured signal generating unit 200 and a theoretical signal is transferred into second input member 420 from theoretical signal generating unit 300 (S410). A difference between the respective measured and theoretical signals is computed in subtraction element 430 to generate respective target skew signals. The target skew signals are then aggregated to form a target skew signal spectrum.

The reliability index is calculated by dividing the reference index by a fitting index, which is defined as an area of the target skew signal spectrum. If the reliability index is within a desired range, the putative thickness is selected as the actual thickness of the target thin layer (S500). The target skew signal spectrum is then processed in skew signal processor 511 to generate the fitting index (S510). Typically, the fitting index comprises the area of the target skew signal spectrum, which can be computed as described as a sum or integral as described previously.

The reliability index is generated in index calculator 512 as a ratio of the reference index and the fitting index (S520). The reliability index is will be referred to as a quality of fitting (QOF), which is defined by the following equation (1):

$$QOF = \text{reference index/fitting index}. \tag{1}$$

Index calculator 512 calculates the reliability index using the reference index in first storage element 110 and the fitting index transferred from skew signal processor 511. As described previously, the reliability index indicates a similarity between the theoretical signal spectrum and the measured signal spectrum. In particular, the reliability index denotes a ratio between the area of the reference skew signal spectrum and the area of the target skew signal spectrum.

The reliability index is compared with a desired range stored in selector 520 (S530). Where the reliability index is within the allowable range, selector 520 selects the putative thickness as the actual thickness of the target thin layer on working wafer "W" (S540) and stores the putative thickness into a buffer in processing unit 500. Where the reliability index is not within the desired range, the putative thickness is updated (S550) and a the theoretical signal spectrum is re-calculated using the updated putative thickness, the refraction index "n" and the extinction coefficient "k" of target thin layer of the wafer "W." Steps S300, S400, and S500 are then repeated until the reliability index is within the desired range. Where the reliability index is within the desired range, the putative thickness is selected as the actual thickness of the target thin layer and is stored into the buffer in processing unit 500.

Where the area of the target skew signal spectrum is smaller than the area of the reference skew signal spectrum so that the reliability index is larger than one, the similarity between the theoretical signal spectrum and the measured signal spectrum is much higher than the similarity between the reference theoretical signal spectrum and the reference measured signal spectrum. Under this circumstance, the area of the target skew signal spectrum is used to replace the reference index in storing unit 100.

The desired range for the reliability index is generally stored in an additional storage element (not shown) in the measurement apparatus. The desired range is then transferred into selector 520 whenever the reliability index is generated. An operator may check the reliability index and the putative thickness whenever each iteration of the regression fitting processes is completed, so that the operator may control the allowable range.

In the exemplary method described in relation to FIGS. 4 through 8, the thickness of the target thin layer is measured by using the reliability index to gauge the similarity between theoretical signal spectrum and the measured signal spectrum.

Figure 1A:
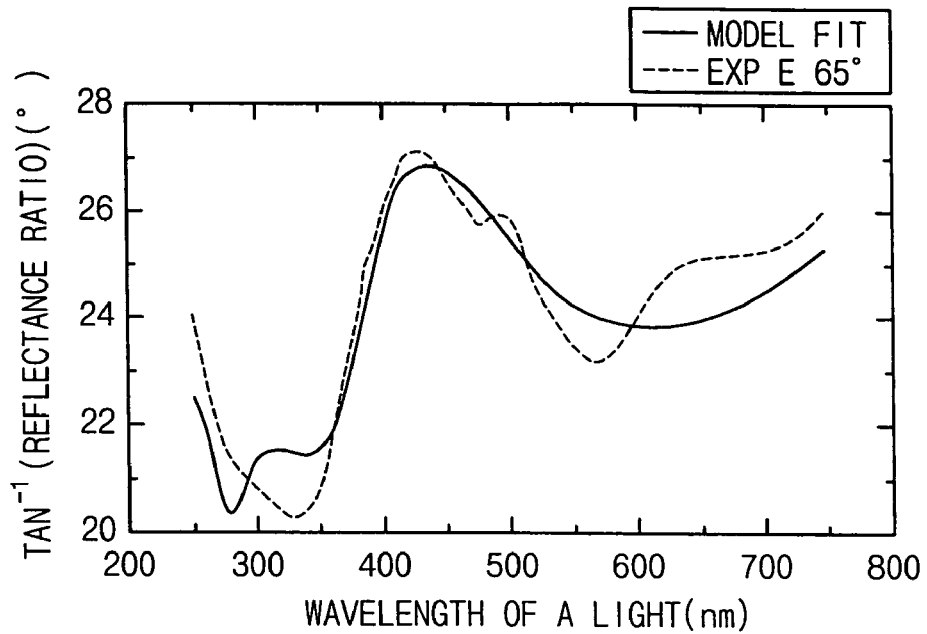
FIGS. 1A and 1B are graphs illustrating a measured signal spectrum and a theoretical signal spectrum used to estimate the thickness of a thin layer in a semiconductor device.
Figure 1B:
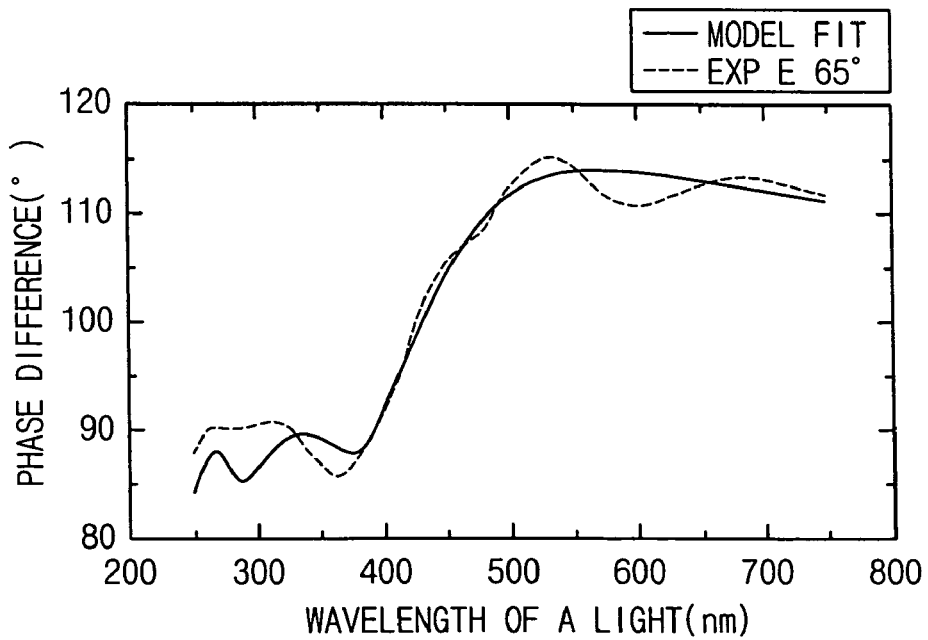
Figure 9A:
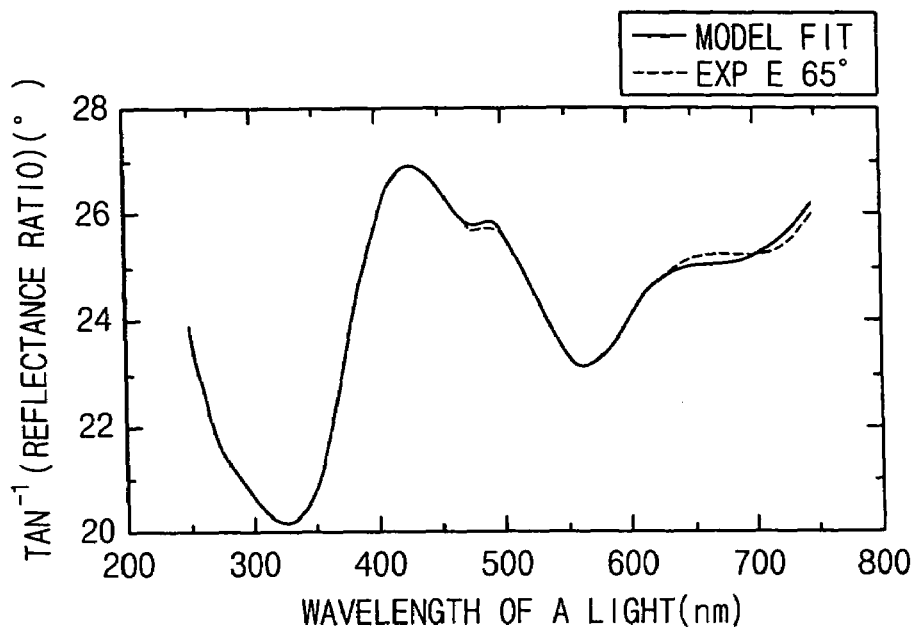
FIG. 9A is a graph illustrating the measured signal shown in FIG. 1A and an optimized theoretical signal similar to the measured signal shown in FIG. 1A.
Figure 9B:
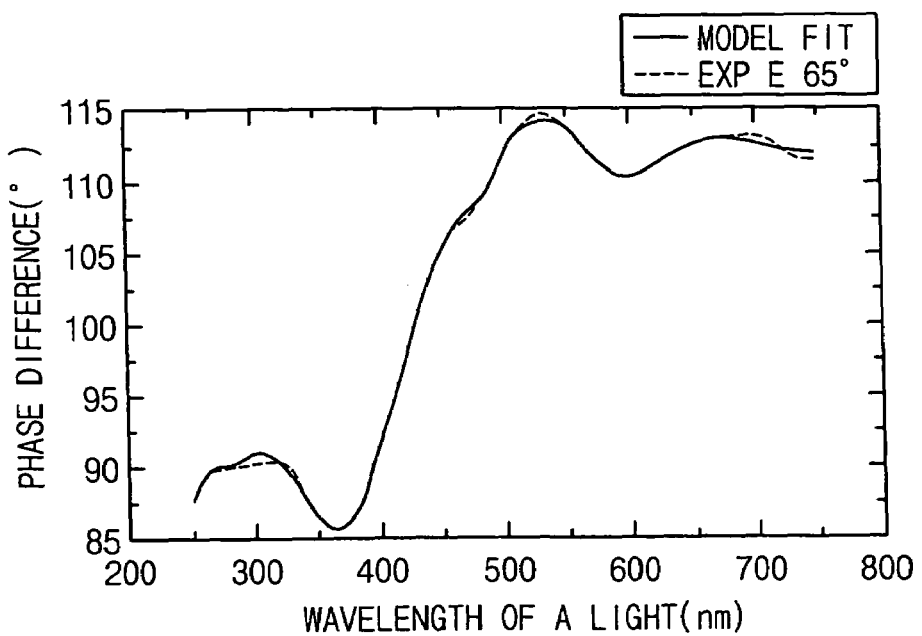
FIG. 9B is a graph illustrating the measured signal shown in FIG. 1B and an optimized theoretical signal similar to the measured signal shown in FIG. 1B.

FIG. 9A is a graph illustrating the measured signal spectrum shown in FIG. 1A and a theoretical signal spectrum generated by a regression fitting process using the reliability index as discussed above. FIG. 9B is a graph illustrating the measured signal spectrum shown in FIG. 1B, and a theoretical signal spectrum generated by a regression fitting process using the reliability index as discussed above. The measured signal spectra shown in FIGS. 9A and 9B were generated under the same conditions as those in FIGS. 1A and 1B.

The GOF value for the measured and theoretical signal spectra shown in FIGS. 9A and 9B is about 0.996. This is similar to the GOF value for the measured and theoretical signal spectra in FIGS. 1A and 1B, which is about 0.976. Since the measured and theoretical signal spectra shown in FIGS. 1A and 1B and significantly less similar than the measured and theoretical signal spectra shown in FIGS. 9A and 9B, GOF values are evidently not a very good measure for the similarity between measured and theoretical signal spectra. In contrast, the area of the target skew signal, as used to generate the theoretical signal spectrum in FIGS. 9A and 9B, is a relatively good indication of the level of similarity between the measured and theoretical signal spectra.

Figure 2:
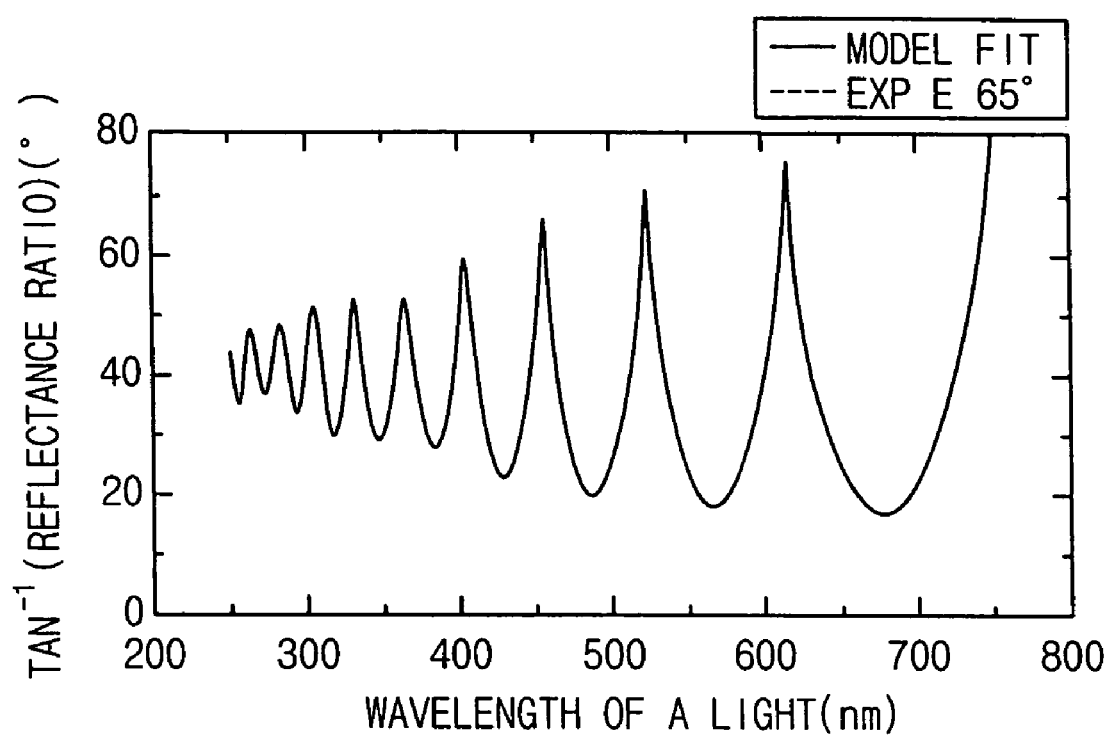
FIG. 2 is a graph illustrating measured and theoretical signal spectra for light reflected from a thin layer formed to a thickness of about 15,000 Å on a wafer.
Figure 3A:
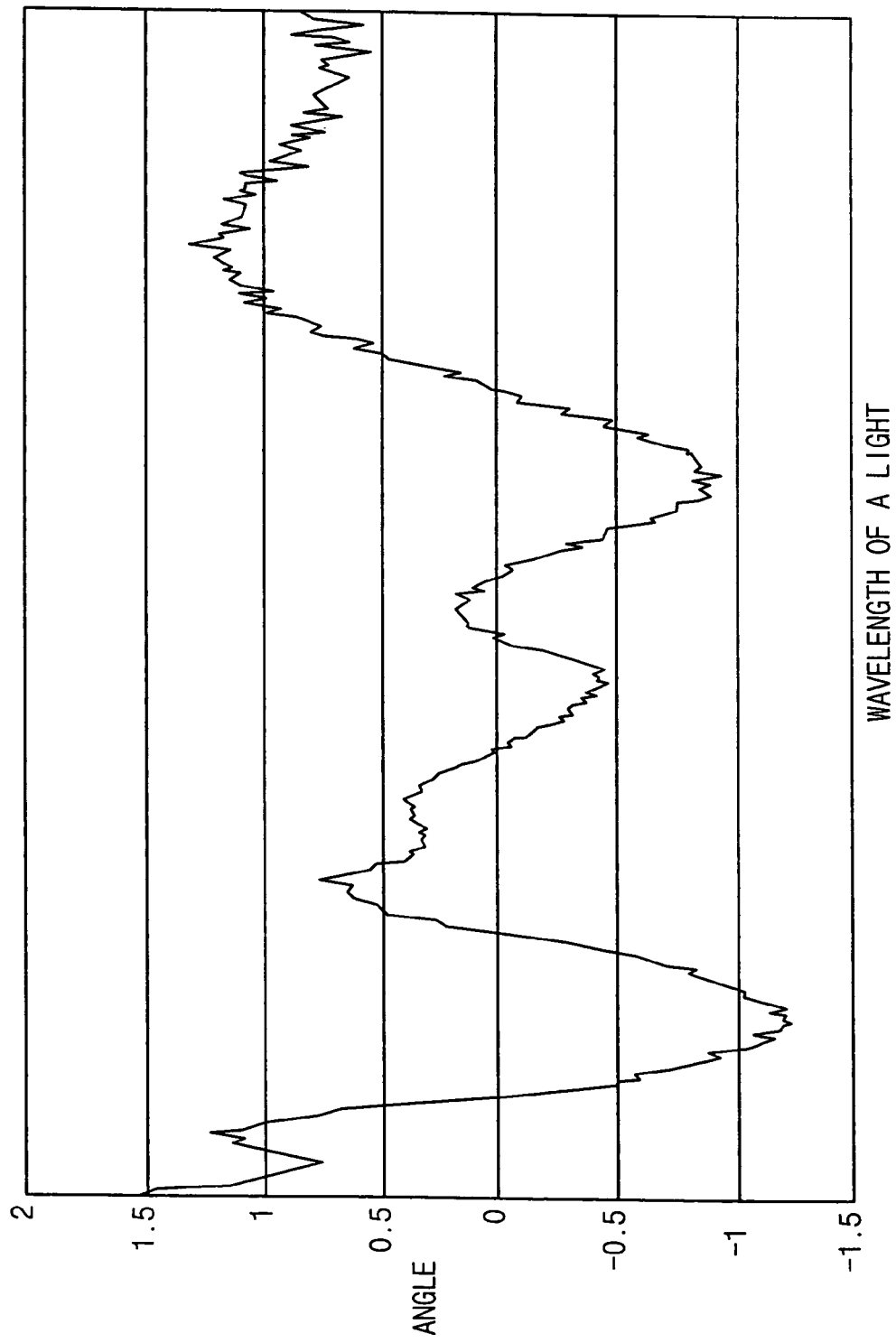
FIG. 3A is a graph illustrating a difference between the measured and theoretical signal spectra shown in FIG. 1A.

FIG. 10A is a graph showing the skew signal spectrum of FIG. 3A (labeled "I"), and a skew signal spectrum for the measured and theoretical signal spectra shown in FIG. 9A (labeled "II"). FIG. 10B is a graph showing a skew signal spectrum corresponding to the measured and theoretical signal spectra shown in FIG. 2B (labeled "I"), and a skew signal spectrum for the measured and theoretical signal spectra shown in FIG. 10B.

Table 1 below shows areas of the spectra I and II shown in FIGS. 10A and 10B. The areas shown in Table 1 were calculated by integrating the spectra shown in FIGS. 10A and 10B.

TABLE 1

| | Spectrum | | | |
| --- | --- | --- | --- | --- |
| | Spectrum I in FIG. 10A | Spectrum I in FIG. 10B | Spectrum II in FIG. 10A | Spectrum II in FIG. 10B |
| Area | 310 | 728 | 36 | 98 |

Although the measured and theoretical signal spectra shown in FIGS. 1A and 1B and 9A and 9B have similar GOF values, the area of their corresponding skew signal spectra are markedly different, as demonstrated by Table 1. Accordingly, the area of the skew signal spectrum is better at distinguishing the level of similarity between the measured and theoretical signal spectra. As a result, the thickness of a thin layer can be more accurately measured by using the reliability index as described above rather than the GOF value.

The following Tables 2 and 3 show measurements of the areas of skew signal spectra that were generated by experiments performed on two different thin layers formed on two different working wafers. In particular, Table 2 relates to measurements performed on a first thin layer on a first wafer, and Table 3 relates to a second thin layer on a second wafer.

In Tables 2 and 3, the term "1st spectrum" is used to denote skew signal spectra generated from a measured signal spectrum defined using the inverse tangent of a reflectance ratio as in FIGS. 1A and 9A, for example. The spectra labeled "1st spectrum, GOF" were generated using the GOF criteria as described above, and the spectra labeled "2nd spectrum, reliability index" were generated using the reliability index, as described above. Within Table 2 both spectra labeled "1st spectrum" were generated using the same measured signal spectrum, and both spectra labeled "2nd spectrum" were generated using the same measured signal spectrum. Similarly, within Table 3 both spectra labeled "1st spectrum" were generated using the same measured signal spectrum, and both spectra labeled "2nd spectrum" were generated using the same measured signal spectrum.

TABLE 2

| | Spectrum | | | |
| --- | --- | --- | --- | --- |
| | 1st spectrum, GOF | 2nd spectrum, GOF | 1st spectrum, reliability index | 2nd spectrum, reliability index |
| Area | 495 | 1257 | 41 | 168 |

TABLE 3

| | Spectrum | | | |
| --- | --- | --- | --- | --- |
| | 1st spectrum, GOF | 2nd spectrum, GOF | 1st spectrum, reliability index | 2nd spectrum, reliability index |
| Area | 310 | 817 | 66 | 184 |

The GOF values for the spectra in Table 2 that were computed using the GOF criteria are about 0.959, and the GOF values for the spectra in Table 2 that were computed using the reliability index is about 0.982. The GOF values for the spectra in Table 3 that were computed using the GOF criteria are about 0.957, and the GOF values for the spectra in Table 3 that were computed using the reliability index is about 0.993. In contrast, the areas shown in Tables 2 and 3 vary significantly depending on whether the GOF criteria or the reliability index is used to generate the theoretical signal spectrum. Thus it can be seen that the reliability index is better able to distinguish the degree of similarity between a theoretical signal spectrum and a measured signal spectrum than the GOF criteria.

One problem with However, the area of the target skew signal spectrum has a problem that a reliability degree of the regression fitting process is varied in accordance with the thickness of the thin layer. When the reliability index of the regression fitting process is only based on the area of the target skew signal spectrum, the reliability index does not provide the same degree of reliability irrespective of the thickness of the thin layer. That is, although the area of the target skew signal spectrum provides more accurate information on the similarity of the theoretical signals than the GOF irrespective of a kind of the thin layer, the reliability index using the area of the target skew signal spectrum is not unique with respect to thickness of the thin layer.

Figure 3B:
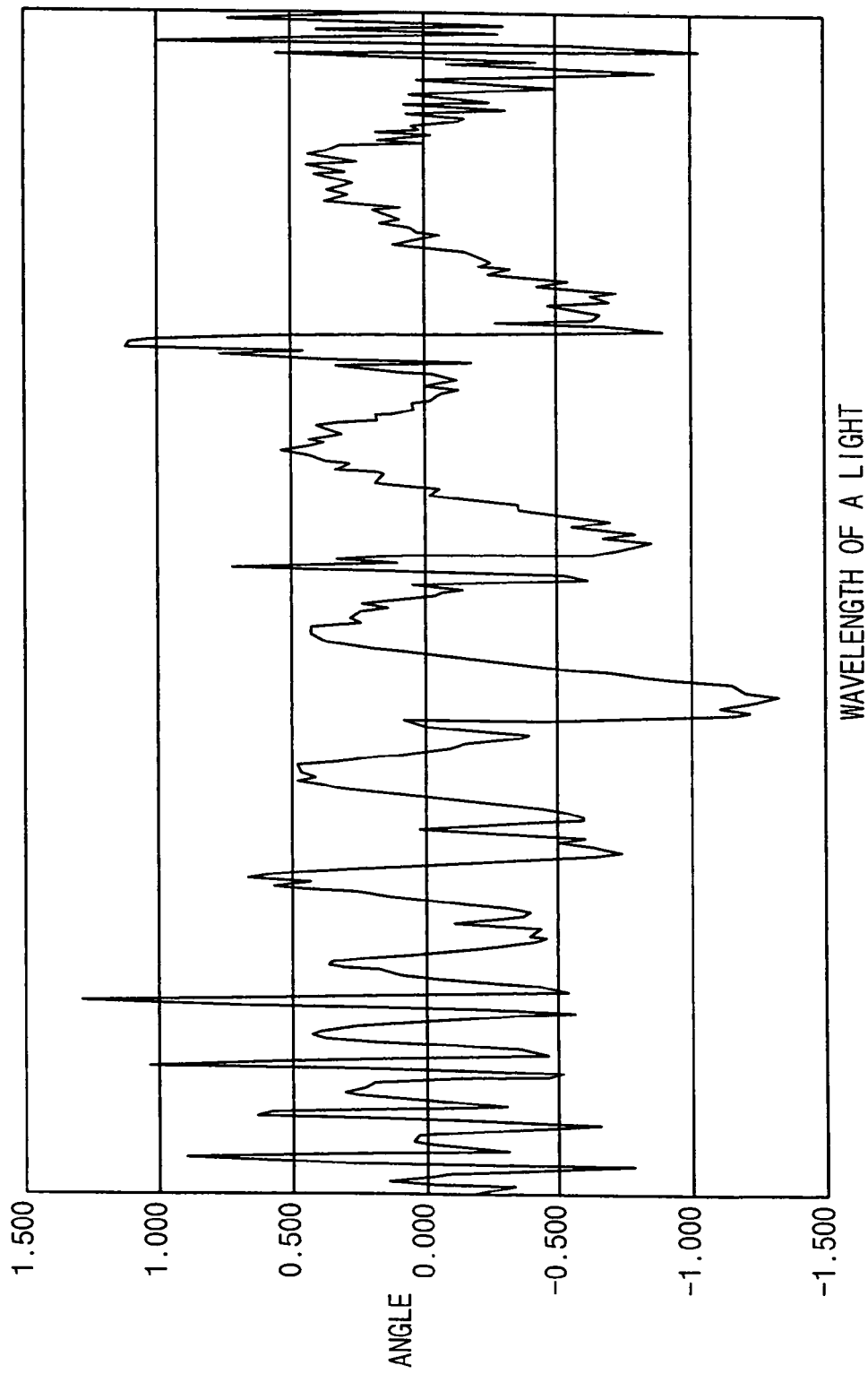
FIG. 3B is a graph illustrating a difference between the measured and theoretical signal spectra shown in FIG. 2.

Table 4 shows the areas and GOF values for the target skew signal spectrum labeled "II" in FIG. 10A and the skew signal spectrum shown in FIG. 3B. These spectra were both generated by the same regression fitting process, i.e., using the reliability index. In addition, these spectra were generated by measurements performed on two different thin layers, and therefore they are respectively labeled "First thin layer" and "Second thin layer" in Table 4. The target skew signal spectrum labeled "II" in FIG. 10A was generated based on measurements of a first thin layer having a thickness of about 1,000 Å and the skew signal spectrum in FIG. 3B was generated based on measurements of a second thin layer having a thickness of about 15,000 Å.

TABLE 4

|  | GOF | Area of the target skew signal spectrum |
|---|---|---|
| First thin layer | 0.996 | 36 |
| Second thin layer | 0.976 | 177 |

Although the same regression fitting process was performed to generate the skew signal spectra for the first and second thin layers relating to Table 4, the GOF of the first thin layer, which has a relatively small thickness, is different from that of the second thin layer, which has a relatively large thickness. That is, the GOF tends to vary with the thickness of the target thin layer. In addition, the area of the target skew signal spectrum also tends to vary with the thickness of the target thin layer. The area of the target skew signal tends to vary more than the GOF value as the thickness of the target thin layer changes. Accordingly, there is not necessarily a unique value for the GOF or the area of the target skew signal spectrum that determines a good value of the reliability index for the regression fitting process.

The QOF defined by equation (1), which is a kind of reliability index for the regression fitting process, compensates for the fact that the area of the target skew signal spectrum varies according to the thickness of a thin layer. The compensation is accomplished by dividing the area of the reference skew signal spectrum by the area of the target skew signal spectrum to obtain the QOF. The QOF may then be used as the reliability index for the regression fitting process irrespective of the kind and thickness of the target thin layer on working wafer "W."

Table 5 below shows QOF values and corresponding areas for selected skew signal spectra described in Tables 1, 2, and 3. In particular, the label "Thin layer 1" in Table 5 refers to the spectra labeled "Spectrum I in FIG. 10A" and "Spectrum II in FIG. 10A" in Table 1. The label "Thin layer 2" refers to 1st spectrum in Table 2, and the label "Thin layer 3" refers to the 1st spectrum in Table 3. The reason for the labels "Thin layer 1", "Thin layer 2", and "Thin layer 3" is that the corresponding spectra were generated with respect to three different thin layers: a first thin layer, a second thin layer, and a third thin layer. The QOF values shown in Table 10 were computed as QOF=(reference index/fitting index)×100. The terms "before optimization" and "after optimization" refer to respective areas and QOF values generated using the GOF criteria versus the QOF.

TABLE 5

|  |  | Area of the target skew signal spectrum | QOF |
|---|---|---|---|
| Thin layer 1 | Before optimization | 310 | 11.6129 |
|  | After optimization | 36 | 100 |
| Thin layer 2 | Before optimization | 495 | 8.282828 |
|  | After optimization | 41 | 100 |
| Thin layer 3 | Before optimization | 310 | 21.29 |
|  | After optimization | 66 | 100 |

In Table 5, the first thin layer, the second thin layer, and the third thin layer were formed on respective wafers under different processing conditions. Based on the areas shown in Table 5, it is difficult to tell which skew signal spectrum corresponds to the most similar measured and theoretical signal spectra. However, the QOF values indicate that thin layer 3 has the most similar measured and theoretical signal spectra before optimization. The next most similar is Thin layer 1, and the most dissimilar measured and theoretical signal spectra prior to optimization is are from Thin layer 2.

According to selected embodiments of the present invention, a QOF value based on the area of the target skew signal spectrum is used as a termination criteria for a regression fitting process in place of a GOF value. Using the QOF value makes the regression fitting process more accurate, and it also decreases the dependency of the regression fitting process's accuracy on the thickness or type of a target thin layer. Accordingly, using the QOF value allows for more accurate measurements of the thickness of layers in the semiconductor devices.

The foregoing preferred embodiments are teaching examples. Those of ordinary skill in the art will understand that various changes in form and details may be made to the exemplary embodiments without departing from the scope of the present invention as defined by the following claims.

What is claimed is:

1. A method of measuring a thickness of a target thin layer formed on a substrate, the method comprising:
   generating a reference skew signal spectrum by performing a regression fitting process on data produced with respect to a reference thin layer formed on a reference layer;
   generating a reference index by processing the reference skew signal spectrum;

generating a measured signal spectrum by irradiating a first light off of the target thin layer to produce a first reflected light, and then analyzing the first reflected light;

generating a theoretical signal spectrum based on a putative thickness of the target thin layer and physical properties of the target thin layer;

generating a target skew signal spectrum as a difference between the measured signal spectrum and the theoretical signal spectrum;

computing a reliability index based on the reference index and the target skew signal spectrum;

determining whether the reliability index is within a predetermined first desired range; and, selecting the putative thickness of the target thin layer as an actual thickness of the target thin layer if the reliability index is within the first desired range.

2. The method of claim 1, wherein generating the reference skew signal spectrum comprises:
(a) generating a reference measured signal spectrum by irradiating a second light off of the reference thin layer to produce a second reflected light and then analyzing the second reflected light;
(b) generating a theoretical signal spectrum by performing a theoretical computation based on a putative thickness of the reference thin layer and physical properties of the reference thin layer;
(c) computing a difference between the reference measured signal spectrum and the reference theoretical signal spectrum; and,
(d) if the difference between the reference measured signal spectrum and the reference theoretical signal spectrum is within a second desired range, updating the putative thickness of the reference thin layer and repeating (b) and (c) until the difference between the reference measured signal spectrum and the reference signal spectrum is within the second desired range.

3. The method of claim 2, wherein the second desired range is determined by a goodness of fit (GOF) value indicating a degree of similarity between the reference measured signal spectrum and the reference theoretical signal spectrum.

4. The method of claim 1, wherein the first light comprises polarized light, and the measured and theoretical signal spectra are computed using an inverse tangent of a reflectance ratio $\tan^{-1}\psi$ of vertical and horizontal components of the polarized light and a phase difference $\Delta$ between the vertical and horizontal components of the polarized light.

5. The method of claim 1, wherein generating the target skew signal spectrum comprises:
transferring a plurality of measured signals and theoretical signals to a skew generating unit; and,
subtracting an intensity of each of the theoretical signals from an intensity of a corresponding one of the measured signals.

6. The method of claim 1, wherein selecting the putative thickness of the target thin layer as an actual thickness of the target thin layer comprises:
generating a fitting index by processing the target skew signal spectrum;
generating the reliability index as a ratio of the reference index and the fitting index;
comparing the reliability index with the first desired range; and,
storing the putative thickness as the actual thickness of the object thin layer if the reliability index is within the desired range.

7. The method of claim 6, wherein generating the reference index by processing the reference skew signal spectrum comprises computing the area of the reference skew signal spectrum; and,
wherein generating the fitting index by processing the target skew signal spectrum comprises computing the area of the target skew signal spectrum.

8. The method of claim 7, wherein computing the area of the reference skew signal spectrum comprises integrating the reference skew signal spectrum over an integration interval covering several wavelengths of light; and,
wherein computing the area of the target skew signal spectrum comprises integrating the target skew signal spectrum over the integration interval.

9. The method of claim 6, further comprising:
(a) if the reliability index is not within the first desired range, modifying the putative thickness of the target thin layer and re-generating the theoretical signal spectrum using the modified putative thickness of the target thin layer;
(b) re-generating the target skew signal spectrum and the fitting index based on the re-generated theoretical signal spectrum; and,
(c) repeating (a) and (b) until the reliability index is within the first desired range.

10. The method of claim 6, further comprising:
if the reliability index is larger than one, storing the fitting index as the reference index.

11. The method of claim 1, wherein the measured signal spectrum is generated through measurements performed by a spectroscopic ellipsometer.

12. An apparatus for measuring a thickness of a target thin layer formed on a substrate, the apparatus comprising:
a storing unit adapted to store recipe data including a reference index and a putative thickness of the target thin layer, wherein the reference index is derived from a regression fitting process performed on data obtained with respect to a reference thin layer formed on a reference wafer;
a measured signal generating unit adapted to generate a measured signal spectrum by irradiating a first light on the target thin layer to produce a first reflected light and analyzing the first reflected light;
a theoretical signal generating unit adapted to generate a theoretical signal spectrum using a theoretical calculation whose inputs include a putative thickness of the target thin layer;
a skew generating unit adapted to generate a target skew signal spectrum as a difference between the measured signal spectrum and the theoretical signal spectrum; and,
a processing unit comprising a processing element adapted to calculate a reliability index from the target skew signal spectrum and the reference index, and a selector adapted to select the putative thickness of the target thin layer as an actual thickness of the target thin layer when the reliability index is within an predetermined desired range.

13. The apparatus of claim 12, wherein the storing unit comprises:
a first storage element adapted to store the reference index; and,
a second storage element adapted to store physical properties of the target thin layer.

14. The apparatus of claim 13, wherein the physical properties include a refractive index of the target thin layer and an extinction coefficient of the target thin layer.

15. The apparatus of claim 12, wherein the substrate comprises a working wafer, and wherein the measured signal generating unit comprises:
- a support adapted to support the working wafer;
- a light source adapted to generate the first light; and,
- a signal generator adapted to detect the first reflected light and generate the measured signal spectrum.

16. The apparatus of claim 15, wherein the measured signal generating unit further comprises a polarizer for polarizing the first light, and the signal generator generates an inverse tangent of a reflectance ratio $\tan^{-1}\psi$ of vertical and horizontal components of the polarized light and a phase difference $\Delta$ between the vertical and horizontal components of the polarized light as a measured signal forming part of the measured signal spectrum.

17. The apparatus of claim 15, wherein the signal generator generates a reflectance of the light as a measured signal forming part of the measured signal spectrum.

18. The apparatus of claim 12, wherein the skew generating unit comprises:
- an input element adapted to receive a measured signal from the measured signals generating unit and a theoretical signal from the theoretical signal generating unit; and,
- a subtraction element adapted to subtract the theoretical signal from the measured signal to generate a target skew signal, wherein the measured signal is part of the measured signal spectrum, the theoretical signal is part of the theoretical signal spectrum, and the target skew signal is part of the target skew signal spectrum.

19. The apparatus of claim 12, wherein the processing unit comprises:
- a skew signal processor adapted to generate a fitting index by processing the target skew signal spectrum; and,
- an index calculator adapted to generate the reliability index using the reference index and the fitting index.

20. The apparatus of claim 19, wherein the reference index is computed as an area of a reference skew signal spectrum;
- wherein the fitting index is computed as an area of the target skew signal spectrum; and,
- wherein the reference skew signal spectrum is computed as a difference between a reference measured signal spectrum and a reference theoretical signal spectrum, both generated with respect to the reference thin layer.

21. The apparatus of claim 20, wherein the skew signal processor comprises:
- an integrator adapted to compute an area of the reference skew signal spectrum and an area of the target skew signal spectrum.

22. The apparatus of claim 20, wherein the reliability index is computed by dividing the reference index by the fitting index.

23. The apparatus of claim 20, further comprising:
- a skew transfer unit adapted to transfer the fitting index to the storing unit where the reliability index is greater than one.

* * * * *